US011571337B2

(12) United States Patent
Töykkälä et al.

(10) Patent No.: US 11,571,337 B2
(45) Date of Patent: Feb. 7, 2023

(54) EAR CUP ASSEMBLY FOR A HEARING PROTECTOR

(71) Applicant: SAVOX COMMUNICATIONS OY AB (LTD), Espoo (FI)

(72) Inventors: Ari-Pekka Töykkälä, Turku (FI); Mikael Lamberg, Helsinki (FI)

(73) Assignee: SAVOX COMMUNICATIONS OY AB (LTD), Espoo (FI)

( * ) Notice: Subject to any disclaimer, the term of this patent is extended or adjusted under 35 U.S.C. 154(b) by 273 days.

(21) Appl. No.: 16/767,816

(22) PCT Filed: Nov. 23, 2018

(86) PCT No.: PCT/FI2018/050852
§ 371 (c)(1),
(2) Date: May 28, 2020

(87) PCT Pub. No.: WO2019/106231
PCT Pub. Date: Jun. 6, 2019

(65) Prior Publication Data
US 2021/0000651 A1 Jan. 7, 2021

(30) Foreign Application Priority Data
Nov. 29, 2017 (FI) .................................. 20176072

(51) Int. Cl.
*H04R 25/00* (2006.01)
*A61F 11/14* (2006.01)
*H04R 1/10* (2006.01)

(52) U.S. Cl.
CPC ............ *A61F 11/14* (2013.01); *H04R 1/1008* (2013.01); *H04R 1/1083* (2013.01); *A61F 11/145* (2022.01)

(58) Field of Classification Search
CPC ...... H04R 1/1008; H04R 1/028; H04R 1/105; H04R 1/1041
See application file for complete search history.

(56) References Cited

U.S. PATENT DOCUMENTS 3,051,961 A 9/1962 Clark
4,057,856 A 11/1977 Aho
(Continued)

FOREIGN PATENT DOCUMENTS

CN 1172423 A 4/2004
CN 102014327 A 4/2011
(Continued)

OTHER PUBLICATIONS

International Search Report and Written Opinion issued by the International Searching Authority (ISA/EP) in PCT Application No. PCT/FI2018/050852 dated Jan. 29, 2019. 11 pages.
(Continued)

*Primary Examiner* — Amir H Etesam
(74) *Attorney, Agent, or Firm* — Meunier Carlin & Curfman LLC

(57) ABSTRACT

According to an aspect of the present disclosure, an ear cup assembly for a hearing protector is provided. In accordance with an example, the ear cup assembly comprises an outer casing, a sealing ring detachably attached on the rim of the outer casing and suitable for sealingly abut against the head of a user around an ear of the user, and a user operable release mechanism for loosening the sealing ring from the outer casing, said release mechanism arranged within the outer casing.

7 Claims, 4 Drawing Sheets

(56) References Cited

U.S. PATENT DOCUMENTS

| | | | |
|---|---|---|---|
| 10,187,715 B2 * | 1/2019 | Karacal | H04R 1/1008 |
| 2008/0128198 A1 * | 6/2008 | Du | A61F 11/14 |
| | | | 181/129 |
| 2012/0205036 A1 | 8/2012 | Huang | |
| 2017/0245787 A1 | 3/2017 | Brown et al. | |

FOREIGN PATENT DOCUMENTS

| | | |
|---|---|---|
| CN | 101472541 B | 6/2012 |
| CN | 205123957 U | 3/2016 |
| GB | 1303612 A1 | 1/1973 |
| JP | H105197 A | 1/1998 |
| WO | 97/48296 A1 | 12/1997 |

OTHER PUBLICATIONS

Search Report issued by the Finnish Patent and Registration Office in Application No. FI 20176072 dated Jul. 26, 2018. 1 page.
International Preliminary Report on Patentability issued by the International Preliminary Examining Authority in PCT Application No. PCT/FI2018/050852 dated Oct. 31, 2019. 15 pages.

\* cited by examiner

EAR CUP ASSEMBLY FOR A HEARING PROTECTOR

CROSS-REFERENCE TO RELATED APPLICATIONS

This application is a national stage application filed under 35 U.S.C. § 371 of PCT/FI2018/050852 filed Nov. 23, 2018, which claims priority to and benefit of Finnish patent application serial number 20176072 filed Nov. 29, 2017, which is fully incorporated by reference and made a part hereof.

FIELD OF THE INVENTION

The present invention relates to an ear cup assembly for a hearing protector and to a hearing protector making use at least one such ear cup assembly.

BACKGROUND

An ear cup for a hearing protector typically comprises an outer casing and a sealing ring arranged on the rim of the outer casing. The sealing ring typically comprises soft and flexible material that makes it suitable for sealingly abut against the head of a user around an ear of the user. The outer casing serves to house noise-damping material that facilitates attenuation of environmental noises. In modern hearing protectors the ear cup typically also comprises electrical components that may be employed e.g. to provide a signal processing system for processing an electrical audio signal obtained from a microphone that is arranged to capture voice signals outside the ear cup. The signal processing system may comprise, for example, a filter for filtering the electrical audio signal and an earphone for producing a sound in response to the filtered electrical audio signal. The filter can be adapted to attenuate impulse noise and/or to attenuate signal components which do not belong to a desired frequency band, e.g. to the frequency band of speech.

Design of the ear cup of a hearing protector is critical for sufficient attenuation of environmental noises. For example, any holes or openings in the outer casing should be minimized to avoid environmental noise leaking inside the casing, and the sealing ring should enable sufficient sealing between itself and the head of the user to avoid environmental noises leaking inside the ear cup between the sealing ring and the head of the user. Yet further, the attachment between the outer casing and the sealing ring should be sufficiently tight to avoid environmental noises leaking inside the ear cup between the sealing ring and the outer casing.

In some scenarios, in an advantageous ear cup design the sealing ring is detachably attached to the outer casing. Detaching the sealing ring for cleaning enables convenient maintenance of the sealing ring to ensure sufficient hygiene, while it also reduces the risk of the inadvertently damaging the electronics provided inside the ear cup while cleaning the sealing ring. Moreover, the possibility to detach and attach the sealing ring enables replacing a worn or damaged sealing ring with a new one to maintain sufficient hygiene, user comfort and/or sealing against the user's head. Yet further, the possibility to detach and attach the sealing ring enables improved hygiene for hearing protectors that are provided for shared use for a plurality of users, e.g. such that each user has his/her own pair of sealing rings for attachment to the ear cups of the hearing protector when needed.

In known designs, the attachment between the outer casing and the sealing ring is provided by a straightforward press fit that provides sufficient force to ensure desired extent (acoustical) sealing between the outer casing and the sealing ring. While the press fit makes detaching and attaching the sealing ring in principle a straightforward operation that can be carried out by the user himself/herself, such design requires careful trade-off between sufficiently tight fit to ensure proper (acoustical) sealing between the outer casing and the sealing ring and sufficiently loose fit to enable convenient detaching and attaching of the sealing ring. Consequently, typically the required extent of (acoustical) sealing results in an arrangement where substantial effort is required for detaching the sealing ring. Since the size of the ear cup is relatively small, detaching the sealing ring using fingers only might be difficult and the user may be tempted to apply tools (such as a screw-driver) in the process, which in turn risks damaging the electronics inside the ear cup, damaging the sealing ring and/or damaging the outer casing.

SUMMARY

In the following a simplified summary of some embodiments of the present invention is provided in order to facilitate a basic understanding of some aspects of the present invention. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

In accordance with a first aspect of the invention, there is provided a novel ear cup assembly for a hearing protector, the ear cup assembly comprising an outer casing, a sealing ring detachably attached on the rim of the outer casing and suitable for sealingly abut against the head of a user around an ear of the user, and a user operable release mechanism for loosening the sealing ring from the outer casing, said release mechanism arranged within the outer casing.

In accordance with a second aspect of the invention, there is provided a novel hearing protector that comprises a first ear cup, a second ear cup, and a band for mechanically interconnecting the first ear cup and the second ear cup, wherein the first and second ear cups are respective ear cup assemblies according to first aspect of the invention.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

The verbs "to comprise" and "to include" are used in this document as open limitations that neither exclude nor require the existence of also un-recited features. The features recited in dependent claims are mutually freely combinable unless otherwise explicitly stated. Furthermore, it is to be understood that the use of "a" or "an", i.e. a singular form, throughout this document does not exclude a plurality.

BRIEF DESCRIPTION OF DRAWINGS

Non-limiting exemplifying embodiments of the present invention and some of their advantages are explained in greater detail in the following with references to the accompanying drawings, in which.

DETAILED DESCRIPTION OF NON-LIMITING EXAMPLE EMBODIMENTS

Figure 1A:
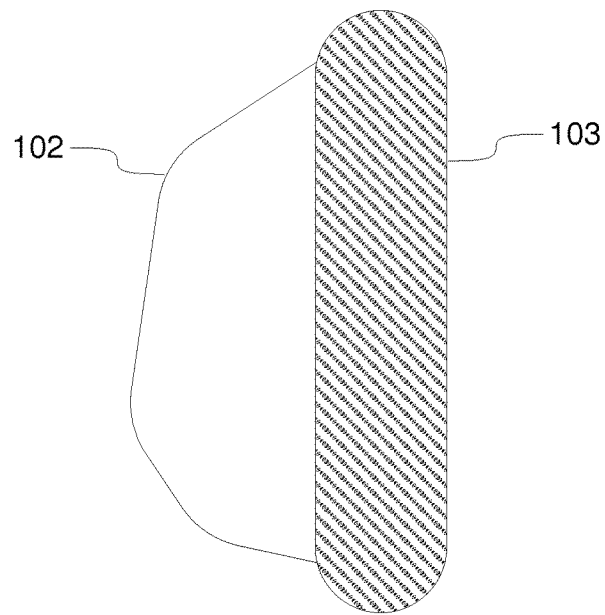
FIGS. 1A, 1B and 1C schematically illustrate an ear cup assembly according to an example.

FIG. 1A schematically illustrates a side view of an ear cup 101 according to an example. The ear cup 101 comprises an outer casing 102 and a sealing ring 103 on the rim of the outer casing 102. The sealing ring 103 is suitable for sealingly abut against the head of a user around an ear of the user. The sealing ring 103 is detachably attached on the rim of the outer casing 102. The attachment between the outer casing 102 and the sealing ring 103 is provided by press fit at a sufficient force that ensure desired extent acoustical sealing between the outer casing 102 and the sealing ring 103, thereby avoiding leakage of environmental noises inside the ear cup between the outer casing 102 and the sealing ring 103 when the sealing ring 103 is attached to the outer casing 102.

The outer casing 102 has a cup-like overall shape and it is typically made of plastic to ensure durable and substantially rigid construction that also allows secure attachment of the sealing ring 103 on its rim by the press fit. As a few non-limiting examples, the outer casing 102 may be made of or may comprise one of the following materials: acrylonitrile butadiene styrene (ABS), polycarbonate (PC), a blend of ABS and PC (ABS/PC), polyamide 6 (PA6) a.k.a. nylon 6, polyamide 66 (PA66) a.k.a. nylon 66, polyoxymethylene (POM).

The sealing ring 103 may be comprise as a substantially rigid fitting portion for securing the sealing ring 103 to the outer casing 102 and a padding portion arranged to cover that side of the fitting portion that is intended to face the head of the user. The fitting portion is provided with an arrangement that has a shape and size that substantially match those of the rim of the outer casing 102, thereby facilitating secure press fit between the sealing ring 103 and the outer casing 102. In one example, the outer perimeter of the fitting portion has a shape and size that substantially match the shape and size of the rim of the outer casing 102 such that the perimeter of the fitting portion is slightly smaller in size/diameter than the those of the rim of the outer casing 102. In another example, the fitting portion is provided with a protrusion that has a shape and size that substantially match the shape and size of the rim of the outer casing 102 such that the outer perimeter of the protrusion is slightly smaller in size/diameter than the those of the rim of the outer casing 102 or such that the inner perimeter of the protrusion is slightly larger in size/diameter than the those of the rim of the outer casing 102.

The fitting portion may be made of plastic to ensure durable and substantially rigid construction that also allows secure attachment to the rim of the outer casing 102 by the press fit. In an example, the fitting portion (and/or the protrusion possibly included therein) is made of the same material as the outer casing 102 to ensure secure fit e.g. regardless of temperature changes. In other examples, the fitting portion (and/or the protrusion possibly included therein) is made of a material that is different from that of the outer casing but that has a thermal expansion coefficient that is the same as or close to that of the material of the outer casing 102. As a few non-limiting examples, the fitting portion (and/or the protrusion possibly included therein) may be made of or may comprise one of the following materials: ABS, PC, ABS/PC, PA6, PA66, POM.

The padding portion typically comprises or is made of soft and flexible material that makes it both comfortable to wear and suitable for sealingly abut against the head of a user around an ear of the user. The sealing ring 103 and/or the padding portion thereof may be also referred to as an ear cushion. As non-limiting examples, the padding portion may include polyurethane (PU) foam and/or solid silicone gel to ensure comfortable but fit against the head of a user.

The outer casing 102 serves to house noise-damping material that facilitates attenuation of environmental noises. The outer casing 102 may also house electric circuitry and/or an arrangement of one or more electrical components. As a non-limiting example, the electric circuitry and/or the arrangement of one or more electrical components may be employed to provide a signal processing system for processing an electrical audio signal obtained from a microphone that is arranged to capture voice signals outside the ear cup 101. The signal processing system may comprise, for example, a filter for filtering the electrical audio signal and an earphone for producing a sound in response to the filtered electrical audio signal. The filter can be adapted to attenuate impulse noise and/or to attenuate signal components which do not belong to a desired frequency band, e.g. to the frequency band of speech.

Figure 1B:
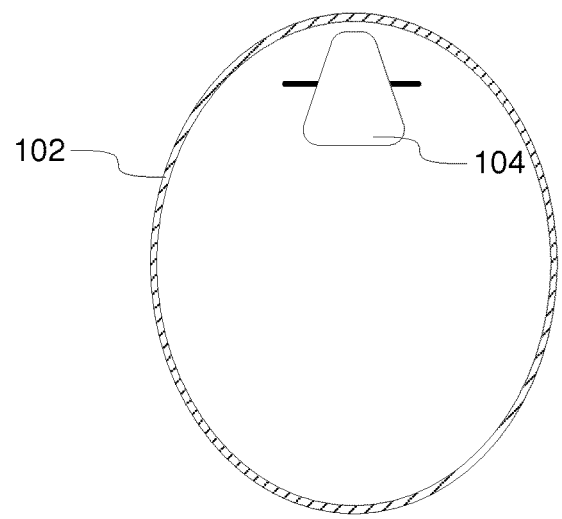

FIG. 1B schematically illustrates the outer casing 102 from the side that is intended to face the sealing ring 103, the illustration of FIG. 1B hence showing the rim of the outer casing 102 (the hatched part) together with the inner side of the outer casing 102 (the solid part inside the hatched part). The illustration of FIG. 1B further shows a user-operable lever arrangement 104 arranged within the outer casing 102. The lever arrangement 104 is provided for loosening the sealing ring 103, when attached thereto, from the outer casing 102. The lever arrangement 104 may be provided inside the outer casing 102 having its hinge fixed to the inner side of the outer casing 102 or to a structure inside the outer casing 102 such that user applying a force (e.g. by pressing) to a first end of a beam of the lever arrangement 104 causes the other end of the beam to push the sealing ring 103 away from the outer casing 102. Hence, operating the lever arrangement 104 results in loosening the sealing ring 103 from the rim of the outer casing 102, thereby facilitating convenient detachment of the sealing ring 103. This, in turn, enables a user to separate the sealing ring 103 from the outer casing 102 with a considerably reduced force, making it easy for the user to detach the sealing ring 103 e.g. using his/her fingers without the need to apply any tools that might risk damaging components of the ear cup 101.

In an example, the lever arrangement 104 (or the beam thereof) is made of suitably rigid plastic material, such as ABS, PC, ABS/PC, PA6, PA66 or POM. In another example, the lever arrangement 104 (or the beam thereof) is made of a suitable metal or metal alloy, such as aluminum, magnesium or stainless steel.

In the example of FIGS. 1A and 1B the release mechanism if represented by the single lever arrangement 104 positioned close to a narrow end of an oval-like or substantially elliptical opening formed by the rim of the outer casing 102. When the ear cup 101 is arranged into an ear cup of a hearing protector, the end of the opening that houses the lever arrangement 104 may be a top end or a bottom end of the opening. In another example, the lever arrangement 104 may be positioned e.g. close to a wide end of the oval-like or substantially elliptical opening formed by the rim of the outer casing 102, such that when the ear cup 101 is arranged into an ear cup of a hearing protector, the end of the opening that houses the lever arrangement 104 may be a front side or the back side of the opening. In another example, the release mechanism may include two lever arrangements 104 arranged inside the outer casing 102 such that they are, for example, positioned at opposite ends of the oval-like or substantially elliptical opening formed by the rim of the outer casing 102. In further example, the release mechanism may include more than two lever arrangements 104 suitably distributed along the rim of the outer casing 102. Inclusion of two or more lever arrangements 104 inside the outer casing 102 enables a release mechanism that induces a higher force in pushing the sealing ring 103 away from the outer casing 102 via operation of the lever arrangements 104, while the downside of such an approach is additional space they require inside the outer casing 102. For example a release mechanism including two lever arrangements 104 at opposite ends of the of the oval-like or substantially elliptical opening formed by the rim of the outer casing 102 may be, however, beneficial in a scenario where the press fit between the outer casing 102 and the sealing ring 103 is especially tight and/or where the opening formed by the rim of the outer casing 102 is relatively large.

The lever arrangement 104 serves a non-limiting example of a release mechanism that is suitable for loosening the sealing ring 103 from the rim of the outer casing 102. Inclusion of the release mechanism such as the lever arrangement 104 inside the outer casing 102 rather than outside thereof is advantageous e.g. in that it enables smaller size and/or leaner design of the outer casing 102 since there is no need to provide possibly bulky release mechanism on the exterior of the ear cup 101. Another advantage that arises from the provision of the release mechanism inside the outer casing 102 readily prevents the user accidentally operating of the release mechanism, which might not be the case for a release mechanism provided on the exterior of the ear cup 101.

Figure 1C:
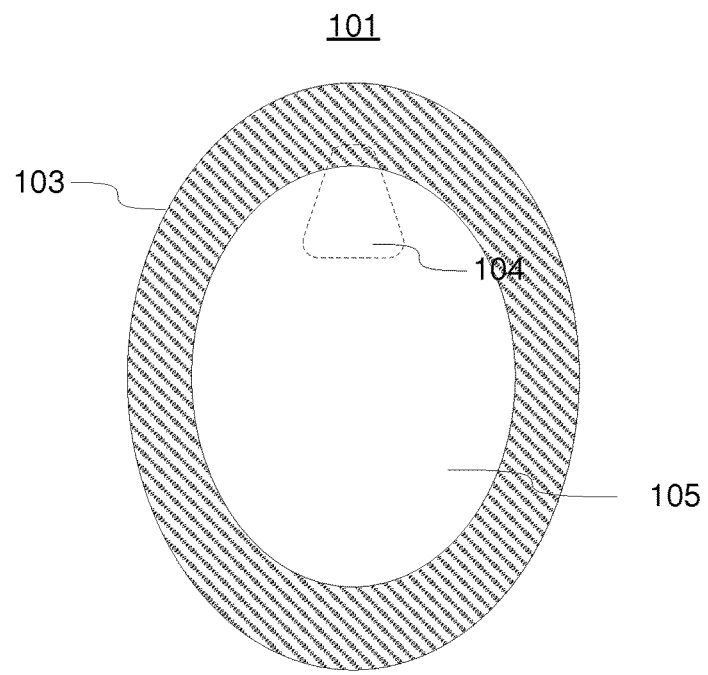

FIG. 1C schematically illustrates the ear cup 101 from the side that is intended to abut against the head of a user around an ear of the user with the sealing ring 103 attached to the outer casing 102. In this regard, the sealing ring 103 includes a recess for accommodating an ear of the user. The illustration of FIG. 1C further shows a cover portion 105 that is arranged to cover the sealing-ring-facing opening of the outer casing 102. The cover portion 105 serves to protect the noise-damping material and electronics possibly arranged inside the outer casing 102 by preventing dust, dirt, moisture, etc. from entering the inner parts of the ear cup 101 and also by preventing direct physical contact between external objects and the components arranged inside the ear cup 101.

The cover portion 105 may be a separate element that is arranged between the outer casing 102 and the sealing ring 103 such that the when attached, the sealing ring 103 secures the cover portion 105 in its position. In another example, the cover portion 105 is integrated with the sealing ring 103 such that when the sealing ring 103 is attached to the rim of the outer casing 102, the cover portion 105 is secured in its position covering the opening of the outer casing 102. In yet another example, the cover portion 105 is integrated with the outer casing 102 such that it serves to cover the sealing-ring-facing opening thereof. The cover portion 105 or the user-facing surface thereof is typically made of soft and flexible material that facilitates conveniently accommodating an ear, thereby contributing to a firm and convenient wearing of the ear cup 101. The cover portion 105 may be provided as or the cover portion 105 may comprise a protective cloth (a protective fabric) and/or a hygienic cloth (a hygienic fabric).

The release mechanism (e.g. the lever arrangement 104 illustrated by using a dashed line in FIG. 1C) that is arranged inside the outer casing 102 is covered by the cover portion 105. Due to flexible characteristic of the cover portion 105 the release mechanism is operable via the cover portion 105. In the example scenario where the release mechanism is provided by the lever arrangement 104 outlined in the foregoing, operation via the cover portion 105 comprises the user applying force to the position of the cover portion 105 that spatially coincides with the first end of the beam, thereby operating the lever arrangement 104 to cause the other end of the beam to push the sealing ring 103 away from the outer casing 102.

In an example, the cover portion 105 is provided with a visual indication at the position that spatially coincides with the release mechanism, e.g. with the first end of the beam of the lever arrangement 104, thereby enabling the user to correctly operate the release mechanism. In another example, the position of the release mechanism 104 under the cover portion 105 is indicated indirectly, e.g. in user manual or usage instructions e.g. provided together with the ear cup 101 or the sealing ring 103 and/or provided in an external source such as a webpage available via the Internet.

Figure 2A:
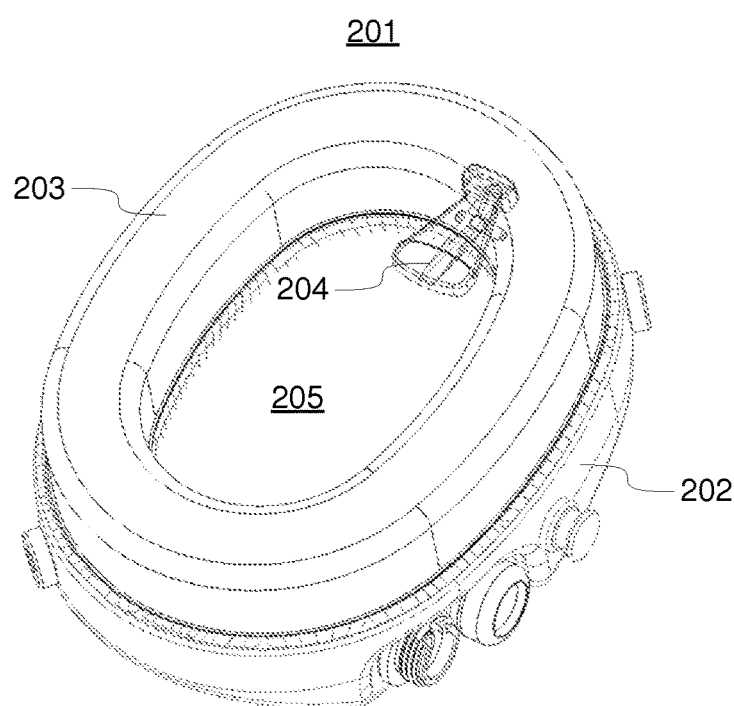
FIGS. 2A and 2B illustrate an ear cup assembly according to an example.
Figure 2B:
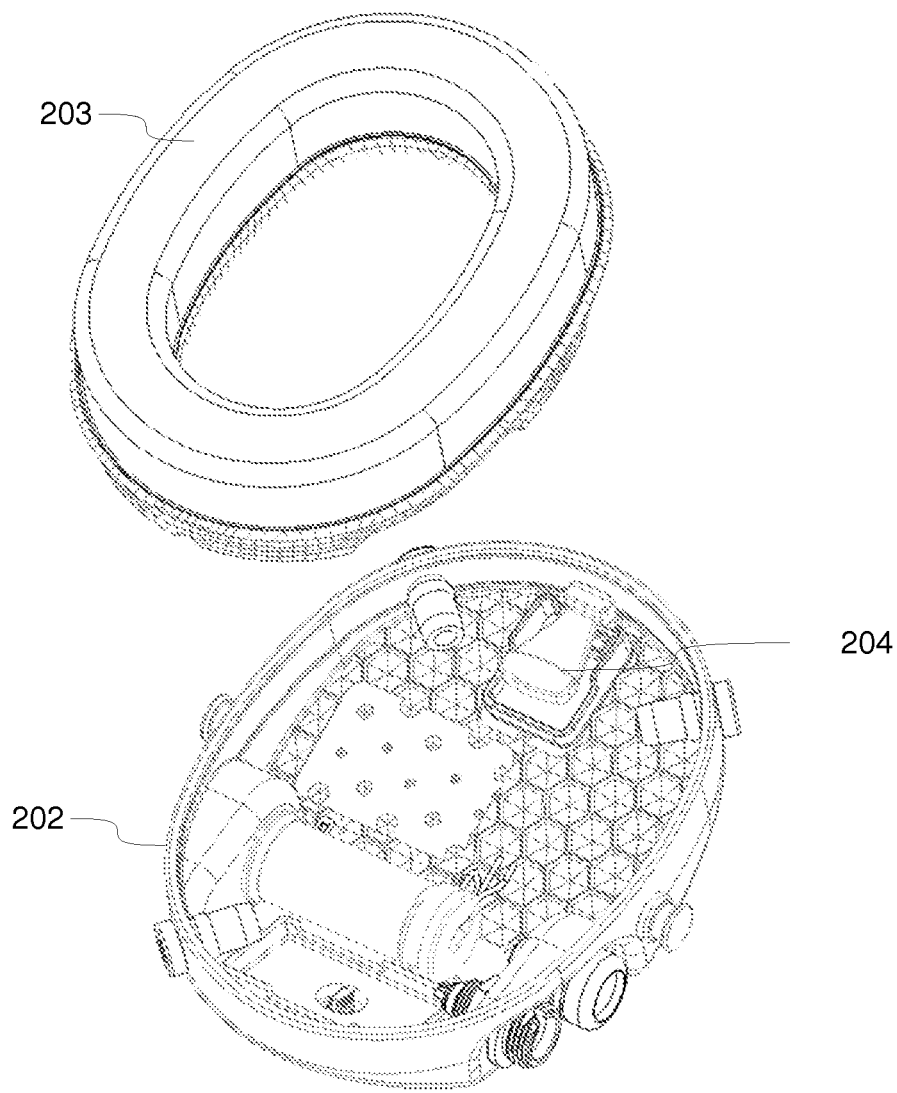

FIG. 2A illustrates some components of an ear cup 201 according to an example embodiment, including an outer casing 202, a sealing ring 203 detachably attached to the rim of the outer casing 202, a lever arrangement 204 arranged inside the outer casing 203 and a cover portion 205 for covering the sealing-ring-facing opening of the outer casing 202. In the illustration of FIG. 2A the lever arrangement 204 that is in reality covered by the sealing ring 203 and the cover portion 205 is shown for visual clarity of the illustration. The outer casing 202, the sealing ring 203, the lever arrangement 204 and the cover portion 205 may be provided as described in the foregoing, respectively, for the outer casing 102, the sealing ring 103, the lever arrangement 104 and the cover portion 105. FIG. 2B illustrates the outer casing 202 and the sealing ring 203 separately from each other. In FIG. 2B, the outer casing 202 is shown with the lever arrangement 204 together with noise-damping material and electrical components arranged therein.

Figure 3:
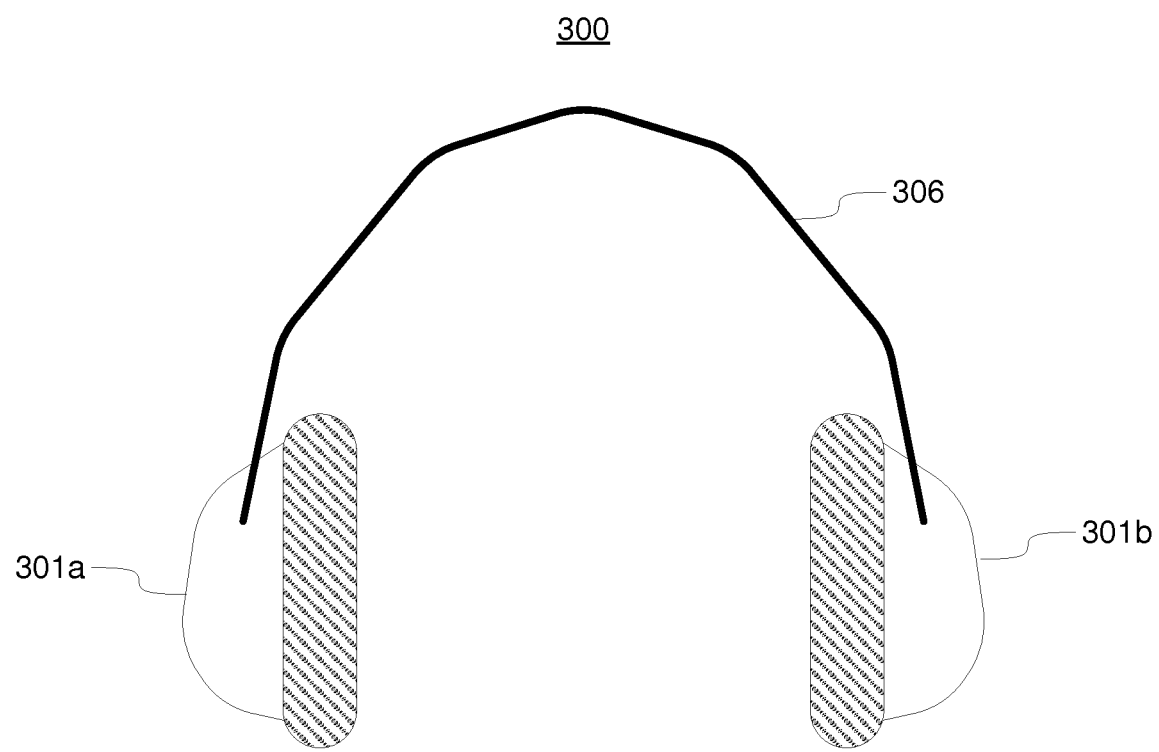
FIG. 3 schematically illustrates a hearing protector according to an example.

FIG. 3 schematically illustrates a hearing protector 300 according to an example. The hearing protector comprises a first ear cup 301a, a second ear cup 301b, and a band 306 for mechanically interconnecting the first ear cup 301a and the second ear cup 301b, where the first and second ear cups 301a, 301b are ear cups according to an embodiment of the invention, such as the ear cup 101 or 201 described in the foregoing.

The specific examples provided in the description given above should not be construed as limiting. Therefore, the present invention is not limited merely to the embodiments described above. Features described in the preceding description may be used in combinations other than the combinations explicitly described. Although functions have been described with reference to certain features, those functions may be performable by other features whether described or not. Although features have been described with reference to certain embodiments, those features may also be present in other embodiments whether described or not.

The invention claimed is:

1. An ear cup assembly for a hearing protector, the ear cup assembly comprising:

an outer casing;
a sealing ring detachably attached on the rim of the outer casing by press fit and suitable for sealingly abutting against the head of a user around an ear of the user; and
a user operable release mechanism for loosening the sealing ring from the outer casing, said release mechanism arranged inside the outer casing and comprising at least one lever arrangement comprising a hinge and a beam, arranged inside the outer casing such that pressing a first end of the beam causes the other end of the beam to push the sealing ring away from the outer casing.

2. The ear cup assembly according to claim 1, wherein the hinge is fixed to an inner side of the outer casing or to a structure provided inside the outer casing.

3. The ear cup assembly according to claim 1, wherein the release mechanism comprises a single lever arrangement positioned at or close to a narrow end of a substantially elliptical opening formed by the rim of the outer casing.

4. The ear cup assembly according to claim 1, wherein the release mechanism comprises two or more lever arrangements positioned at respective locations at or close to the rim of the outer casing.

5. The ear cup assembly according to claim 1, further comprising a flexible cover portion arranged to cover the sealing-ring-facing opening of the outer casing, wherein the release mechanism is operable via the cover portion.

6. The ear cup assembly according to claim 5, wherein the cover portion is provided with a visual indication at a position that spatially coincides with the first end of the beam of the level arrangement.

7. A hearing protector comprising a first ear cup, a second ear cup, and a band for mechanically interconnecting the first ear cup and the second ear cup, wherein the first and second ear cups are respective ear cup assemblies according to claim 1.

* * * * *